United States Patent [19]

Helioff et al.

[11] Patent Number: 5,032,391

[45] Date of Patent: Jul. 16, 1991

[54] HAIR STYLING GEL COMPOSITION

[75] Inventors: Michael W. Helioff, Westfield; Mohammed Tazi, Wayne; Robert B. Login, Oakland, all of N.J.; Yoon T. Kwak, Brooklyn, N.Y.

[73] Assignee: GAF Chemicals Corporation, Wayne, N.J.

[21] Appl. No.: 564,918

[22] Filed: Aug. 9, 1990

[51] Int. Cl.$^5$ .................................................. A61K 7/11
[52] U.S. Cl. ........................................ 424/71; 424/70; 514/944
[58] Field of Search .................... 424/71, 70; 514/944

[56] References Cited

U.S. PATENT DOCUMENTS

| | | | |
|---|---|---|---|
| 4,059,688 | 11/1977 | Rosenberg | 474/47 |
| 4,839,166 | 6/1989 | Grollier | 424/70 |
| 4,897,262 | 1/1990 | Nandagiri | 424/71 |

*Primary Examiner*—Thurman Page
*Assistant Examiner*—Robert H. Harrison
*Attorney, Agent, or Firm*—Walter Katz; Marilyn J. Maue; Joshua J. Ward

[57] ABSTRACT

This invention relates to a hair styling gel containing a neutralized, crosslinked maleic anhydride $C_1$-$C_5$-alkyl vinyl ether copolymer. The formulation is a clear gel of suitable viscosity and pH. This composition provides effective hair styling at low copolymer levels. The favorable characteristics of the composition includes no drag on comb-out and a clean feel on the hair after use.

6 Claims, No Drawings

HAIR STYLING GEL COMPOSITION

BACKGROUND OF THE INVENTION

1. Field of the Invention

This invention relates to hair styling gel compositions and, more particularly, to hair fixative gel compositions containing clear copolymer gels which provide effective hair styling at low compolymers concentrations.

2. Description of the Prior Art

A wide variety of hair styling gels are available for hair fixation, particularly for creating spikes and the like, which can add body and shine to hair without unwanted flaking or dryness. These formulations generally allow the creation of "hair looks" such as the wet or dry looks, to control frizzie perms and natural waves, to provide long lasting blow waves which simulate a non-oil wet look and which when brushed through can create a dry fluffy look.

Accordingly, an object of this invention is to provide an effective and clear hair styling gel composition containing a neutralized, crosslinked maleic anhydride-$C_1$-$C_5$-alkyl vinyl ether gel copolymer of suitable viscosity and pH, which composition is efficient at hair styling at relatively low copolymer concentrations without causing drag on comb-out, which leaves a clean feel upon application, is non-tacky and which can be washed out easily.

These and other objects and features of the invention will be made apparent from the following description.

SUMMARY OF THE INVENTION

What is provided herein is a clear hair styling gel composition containing a neutralized, crossliked maleic anhydride-$C_1$-$C_5$-alkyl vinyl ether gel copolymer of suitable viscosity and pH.

A typical copolymer gel of the invention is a maleic anhydride-methyl vinyl ether copolymer crosslinked with about 1 to 5 mole percent based on the methyl vinyl ether of a crosslinking agent such as 1,9-decadiene or 1,7-octadiene.

The copolymer gel itself includes about 0.5 to 1.5% by weight copolymer, has a viscosity of about 35,000 to 180,000 cps, preferably about 100,000 to 150,000, and is neutralized to a pH of about 4–11, preferably about 6–7.4, and, optimally, about 6.8.

Preferably the composition includes about 65–100% by weight of the copolymer gel solution, most preferably about 80–90%, and, optimally, about 86%. The remaining components of the formulation may include one or more of the following: a polyvinylpyrrolidone (PVP) component, which enhances the fixative properties of the composition, a preservative, a fragrance, a UV absorber and a chelating agent. Water is present in the composition to dissolve the components therein.

The clear hair styling gel composition of the invention provides effective hair fixature properties with enhanced clean feel and shine, even at low copolymer gel levels, without drag on comb-out, oiliness or tackiness.

DETAILED DESCRIPTION OF THE INVENTION

The neutralized, crosslinked maleic anhydride-$C_1$-$C_5$-alkyl vinyl ether copolymer gel of the invention is prepared by polymerizing maleic anhydride, a $C_1$-$C_5$-alkyl vinyl ether and a crosslinking agent in the pres of a suitable free radical initiator.

Different solvents may be used for the polymerization, including benzene, toluene, xylene, acetone, methyl ethyl ketone and methylene chloride; however, it is preferred to use a mixture of a carboxylic acid ester and a saturated cycloaliphatic hydrocarbon. A particularly preferred solvent system is a mixture of ethyl acetate and cyclohexane, preferably in the weight ratio of about 35 to 55% ethyl acetate to about 45 to 65% cyclohexane.

In this solvent system, the crosslinked copolymer product is provided in pumpable slurry form, from which dry, fine, white powders can be obtained easily. The copolymer powders can be readily hydrolyzed to clear gels of high viscosities with good stability and excellent salt tolerance.

The amount of crosslinking agent used in polymerization generally varies from about 1 to about 5 mole percent based on the monovinyl alkyl ether. Examples of suitable crosslinking agents include diunsaturated compounds such as the divinyl ethers of an aliphatic diol, e.g. the divinyl ethers of 1,2-ethanediol; 1,3-propanediol; 1,4-butanediol, 1,5-pentanediol; 1,6-hexanediol; 1,7-heptanediol; 1,8-octanediol; 1,9-nonanediol; 1,10-decanediol; 1,11-undecanediol; and 1,12-dodecanediol, as well as the divinyl ethers of diethylene glycol, triethylene glycol, tetraethylene glycol, pentaethylene glycol; hexaethylene glycol, heptaethylene glycol, octaethylene glycol, nonaethylene glycol, decaethylene glycol and further polyalkylene glycols up to a molecular weight of about 5900. Other suitable crosslinking agents include 1,7-octadiene, 1,9-decadiene, divinylbenzene, N,N'-bis-methylene acrylamide, acrylates such as polyethylene glycol diacrylate, trimethylolpropane triacrylate, propylene glycol diacrylate, polyhydric alcohols esterified once or twice with acrylic acid triallylamine, tetraallylehylenediamine, diallyl phthalate, and the like.

The polymerization is carried out conveniently by preparing the mixed solvent solution of the monomers and adding a catalytic amount (generally from 0.001 to 1.0%) of an organic free radical-generating initiator. The resulting solution then is mixed thoroughly and heated sufficiently so that the polymerization reaction takes place. At the completion of the polymerization reaction, the precipitated interpolymer is isolated by any suitable means such as by filtration or distillation of solvent, then washed with fresh solvent and vacuum dried.

Suitable organic free radical-generating initiators includes azobisisobutyronitrile, benzoyl peroxide, lauroyl peroxide, caprylyl peroxide, acetyl peroxide, acetyl benzoyl peroxide, di-tert-butyl peroxide, t-butyl peroxypivalate, azobis(2,4-dimethyl-valeronitrile) and the like. Mixtures of such catalysts are also suitable in the process of making the interpolymers of the invention.

The polymerization is carried out at a temperature within the range of from 50° to 100° C., particularly about 60°–80° C.

After obtaining the dry powder copolymer, the anhydride groups thereof are hydrolyzed and neutralized in aqueous basic solution at a suitable temperature, e.g. about 60° C. Suitably, a 0.5 to 1.5% by weight copolymer gel is obtained. Typically, about 1 g. of the copolymer is dissolved in about 2.4–3.0 g. of a 10% aqueous NaOH solution and 96–97.6 g. of water. The resultant pH of the clear hydrolyzed and neutralized copolymer is about 4–11, preferably 6–7.4, and, most preferably, about 6.8.

The clear, hydrolyzed and neutralized copolymer is the gel base of the hair styling gel composition of the invention. The viscosity of the gel base is determined at 25° C. with a RTV Brookfield viscometer spindle TE type at RMP 10. Suitable viscosities range from about 35,000 to about 180,000 cps, and, preferably about 100,000 to 160,000. A copolymer gel viscosity of about 150,000 is most preferred for preparing the hair styling gel compositions of the invention.

The remaining ingredients in the composition are to be considered as optional components. However, for practical commercial products, and for effective hair styling action, it is preferred to include PVP, which is a hair fixative resin, in an amount of about 1–5% by weight of the composition, which enhances the fixative properties of the gel base.

A typical formulation of the invention is as follows:

| STYLING GEL COMPOSITION OF INVENTION | | Percent by Weight | |
|---|---|---|---|
| Component | Suitable | Preferred | Optimum |
| Essential | | | |
| Gel Base (1% copolymer) | 65–100 | 80–90 | 86.15 |
| pH | (4–11) | (6–7.4) | (6.8) |
| Viscosity | (35 to 180,000 cps) | (100–160,000) | (150,000) |
| Preferred | | | |
| Deionized water | 0–20 | 5–15 | 10.00 |
| Chelating agent Cheelox BF-13$^a$ | 0–0.5 | 0.05–0.15 | 0.10 |
| UV absorber Uvinul MS-40+ | 0–0.5 | 0.05–0.15 | 0.10 |
| Fixative resin PVP K-30 | 0–8 | 1–5 | 2.50 |
| Preservative Kathon CG* | 0–0.15 | 0.01–0.10 | 0.05 |
| Fragrance Perfume | 0–0.80 | 0.05–0.25 | 0.10 |
| (in Ameroxol OE-10**) | 0–5 | 0.50–2.00 | 1.00 |
| | | | 100.00 |
| pH of composition | 5–8 | 6–7 | 6.5 |
| Viscosity of composition | 25 to 75,000 cps | 40 to 60,000 | 53,000 |

$^a$ethylenediaminetetraacetic acid
*methylchloroisothiazolinone and methylisothiazolinone
**ethoxylated (10 moles) oleyl alcohol
+benzophenone-4

The invention will now be described with reference to the following examples.

EXAMPLE 1

Preparation of Crosslinked Copolymer

A reactor was precharged with a 50:50 weight mixture of ethyl acetate and cyclohexane as a cosolvent composition, and 1,7-octadiene as a crosslinking agent. The reactor was then purged with nitrogen, heated to 58° C., and charged with initiator (Lupersol-11 which is t-butyl peroxypivalate) at a 0.15 to 2% by weight level based on maleic anhydride (MA). Then molten maleic anhydride and methyl vinyl ether (MVE) were fed separately (or through a common inlet) into the reactor over a 2 to 3 hr. period. The reactants were held at that temperature for an additional 1 to 3 hrs., then cooled, vented and discharged. The resulting slurry, in which the copolymer product was present at an 18 to 25% solids level, was filtered and dried. Fine white powders of the desired crosslinked copolymer were obtained.

EXAMPLE 2

Preparation of Hydrolyzed and Neutralized Crosslinked Copolymer 1 g. of the crosslinked copolymer prepared above in 2.7 g. of a 10% aqueous NaOH solution and 96.3 g. of water were heated at 60° C. to form a clear gel base having a viscosity of 150,000 cps, and it was stable at that value at room temperature for an extended period of time.

EXAMPLE 3

Formulation of Hair Styling Gel Composition of Invention

To 86.15 g. of the gel base prepared above was added 0.10 g. of Cheelox BF-13. Then 2.50 g. of PVP K-30 was dissolved in 7 ml. of distilled water, and, additionally 3 ml. of the water was added to 0.10 g. of Uvinul MS-40 and stirred into the gel base. Then 0.05 g. Kathon CG, 0.10 g. of perfume and 1.00 g. of Ameroxol OE-10 fragrance were stirred into the gel base. Finally the PVP solution was stirred in.

EXAMPLE 4

Hair Styling Use of Composition of Invention

In use as a hair styling agent, the clear gel composition of the invention achieved an effective hair look even at the low concentration of the gel component in the formulation. Treated hair has a desirable feel and shine, and longer lasting blow waves are created, as well as, hot roller sets, and curling iron and roller sets. Brushing created a dry fluffing look.

While the invention has been described with particular reference to certain embodiments thereof, it will be understood that changes and modifications may be made which are within the skill of the art. Accordingly, it is intended to be bound only by the following claims, in which:

What is claimed is:

1. A hair styling gel composition comprising about 65 to 100% by weight of a hydrolyzed and neutralized crosslinked maleic anhydride $C_1$–$C_5$-alkyl vinyl ether copolymer gel wherein the copolymer gel includes about 0.5–1.5% by weight of the copolymer therein.

2. A hair styling gel composition according to claim 1 wherein said hydrolyzed and neutralized crosslinked maleic anhydride $C_1$–$C_5$-alkyl vinyl ether copolymer gel has a viscosity of about 35,000 to about 180,000 cps, and a pH of about 4 to 11, and, optionally one or more of the following ingredients: a PVP resin, a chelating agent, a UV absorber, a preservative, a fragrance and deionized water.

3. A hair styling gel composition according to claim 2 wherein said copolymer gel has a viscosity of about 100,000 to 160,000 cps and a pH of about 6–7.4

4. A hair styling gel composition according to claim 1 which includes about 0–20% by weight of deionized water, about 0–8% by weight of a PVP resin, about 0–0.5% by weight of a chelating agent, about 0–0.5% by weight of a UV absorber, about 0–0.15% by weight of a preservative, and a solution of 0–0.80% by weight of a perfume in 0–5% by weight of a solvent, the pH of the composition is about 5–8 and the viscosity of the composition is about 25,000 to 75,000 cps.

5. A hair styling gel composition according to claim 2 comprising about 80-90% by weight of said copolymer gel having a viscosity of about 100,000 to 160,000 and a pH of about 6-7.4, and containing about 1% by weight of said copolymer, about 5-15% weight of deionized water, about 0.5-0.15% by weight of a chelating agent, about 0.05-0.15% by weight of a UV absorber, about 1-5% by weight of PVP, about 0.01-0.10% by weight of a preservative, and about 0.05-0.25% by weight of a perfume in about 0.50-2.0% by weight of a solvent, the pH of the composition being about 6-7, and the viscosity of the composition being about 40,000 to 60,000 cps.

6. A hair styling gel according to claim 2 comprising about 86% by weight of said copolymer gel having a viscosity of about 150,000 and a pH of about 6.8, and containing about 1% by weight of said copolymer, about 10% weight of deionized water, about 0.10% by weight of a chelating agent, about 0.10% by weight of a UV absorber, about 2.50% by weight of PVP, about 0.05% by weight of a preservative, and about 0.10% by weight of a perfume in about 1.00% by weight of a solvent, the pH of the composition being about 6.5, and the viscosity of the composition being about 53,000 cps.

* * * * *